(12) United States Patent
Condie et al.

(10) Patent No.: US 9,750,570 B2
(45) Date of Patent: Sep. 5, 2017

(54) SYSTEMS AND METHODS FOR DETECTING TISSUE CONTACT DURING ABLATION

(71) Applicant: Medtronic Ablation Frontiers LLC, Minneapolis, MN (US)

(72) Inventors: Catherine R. Condie, Shoreview, MN (US); Marshall L. Sherman, Cardiff by the Sea, CA (US); Mark T. Stewart, Lino Lakes, MN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 0 days.

(21) Appl. No.: 14/934,855

(22) Filed: Nov. 6, 2015

(65) Prior Publication Data
US 2016/0058505 A1    Mar. 3, 2016

Related U.S. Application Data (62) Division of application No. 13/460,900, filed on May 1, 2012.

(51) Int. Cl.
*A61B 18/00* (2006.01)
*A61B 18/14* (2006.01)
(Continued)

(52) U.S. Cl.
CPC .......... *A61B 18/1492* (2013.01); *A61B 19/46* (2013.01); *A61B 2018/0022* (2013.01);
(Continued)

(58) Field of Classification Search
CPC ..... A61B 5/053; A61B 5/0536; A61B 5/0538; A61B 5/4887; A61B 5/6869;
(Continued)

(56) References Cited

U.S. PATENT DOCUMENTS

| 5,341,807 A | 8/1994 | Nardella |
| 5,423,808 A | 6/1995 | Edwards et al. |

(Continued)

FOREIGN PATENT DOCUMENTS

| EP | 0703461 A2 | 3/1996 |
| EP | 1151725 A1 | 11/2001 |

(Continued)

OTHER PUBLICATIONS

International Search Report and Written Opinion of the International Searching Authority dated Jul. 1, 2013 for International Application Serial No. PCT/US2013/035896, International Filing Date: Apr. 10, 2013 consisting of 12-pages.

*Primary Examiner* — Eugene T Wu
(74) *Attorney, Agent, or Firm* — Christopher & Weisberg, P.A.

(57) ABSTRACT

Systems and methods for assessing tissue contact, including positioning a plurality of electrodes adjacent a tissue region; delivering radiofrequency energy to the plurality of electrodes, wherein the delivered radiofrequency energy is sufficient to ablate at least a portion of the tissue region; obtaining a plurality of impedance measurements from the plurality of electrodes during the delivery of the radiofrequency energy; calculating a change in the impedance measurements for each of the plurality of electrodes over a pre-determined time period; comparing the calculated change for at least one of the plurality of electrodes to the calculated change in at least one other of the plurality of electrode to determine if there is significant variation in the calculated changes; and terminating the delivery of radiofrequency energy to at least one of the plurality if there is significant variation in the calculated changes.

4 Claims, 5 Drawing Sheets

(51) Int. Cl.
*A61B 19/00* (2006.01)
*A61B 18/02* (2006.01)
*A61B 90/00* (2016.01)

(52) U.S. Cl.
CPC ............... *A61B 2018/00285* (2013.01); *A61B 2018/00345* (2013.01); *A61B 2018/00577* (2013.01); *A61B 2018/00642* (2013.01); *A61B 2018/00708* (2013.01); *A61B 2018/00791* (2013.01); *A61B 2018/00863* (2013.01); *A61B 2018/00875* (2013.01); *A61B 2018/00898* (2013.01); *A61B 2018/0212* (2013.01); *A61B 2018/0262* (2013.01); *A61B 2018/1467* (2013.01); *A61B 2019/465* (2013.01); *A61B 2090/065* (2016.02)

(58) Field of Classification Search
CPC ................ A61B 5/6885; A61B 5/6886; A61B 2018/00375; A61B 2018/00577; A61B 2018/00636; A61B 2018/00642; A61B 2018/00648; A61B 2018/00654; A61B 2018/00666; A61B 2018/00672; A61B 2018/00678; A61B 2018/00875; A61B 2018/00898; A61B 2018/00904
See application file for complete search history.

(56) References Cited

U.S. PATENT DOCUMENTS

| | | | |
|---|---|---|---|
| 5,447,529 A | 9/1995 | Marchlinski et al. | |
| 5,514,129 A | 5/1996 | Smith | |
| 5,598,848 A * | 2/1997 | Swanson | A61B 5/0422 600/374 |
| 5,681,308 A | 10/1997 | Edwards et al. | |
| 5,769,846 A | 6/1998 | Edwards et al. | |
| 5,897,577 A | 4/1999 | Cinbis et al. | |
| 6,050,267 A | 4/2000 | Nardella et al. | |
| 6,132,426 A | 10/2000 | Kroll | |
| 6,162,216 A | 12/2000 | Guziak et al. | |
| 6,203,541 B1 | 3/2001 | Keppel | |
| 6,217,574 B1 | 4/2001 | Webster | |
| 6,256,540 B1 | 7/2001 | Panescu et al. | |
| 6,391,024 B1 * | 5/2002 | Sun | A61B 18/1206 606/34 |
| 6,546,270 B1 | 4/2003 | Goldin et al. | |
| 6,648,883 B2 | 11/2003 | Francischelli et al. | |
| 6,730,079 B2 | 5/2004 | Lovewell | |
| 7,736,357 B2 | 6/2010 | Lee, Jr. et al. | |
| 8,398,626 B2 | 3/2013 | Buysse et al. | |
| 2002/0032439 A1 | 3/2002 | Hareyama | |
| 2003/0220636 A1 * | 11/2003 | Bowman | A61B 18/1492 606/28 |
| 2004/0064161 A1 | 4/2004 | Gunderson et al. | |
| 2005/0090815 A1 * | 4/2005 | Francischelli | A61B 18/1206 606/32 |
| 2005/0222562 A1 | 10/2005 | Lovewell | |
| 2005/0283074 A1 | 12/2005 | Jackson et al. | |
| 2007/0062547 A1 * | 3/2007 | Pappone | A61B 18/1233 128/898 |
| 2007/0173808 A1 | 7/2007 | Goble | |
| 2007/0255162 A1 | 11/2007 | Abboud et al. | |
| 2008/0281312 A1 | 11/2008 | Werneth et al. | |
| 2008/0281314 A1 | 11/2008 | Johnson et al. | |
| 2009/0030664 A1 | 1/2009 | Bridges et al. | |
| 2009/0157071 A1 | 6/2009 | Wham et al. | |
| 2009/0240244 A1 | 9/2009 | Malis et al. | |
| 2009/0275827 A1 | 11/2009 | Aiken et al. | |
| 2010/0049188 A1 | 2/2010 | Nelson et al. | |
| 2010/0069921 A1 * | 3/2010 | Miller | A61B 18/1233 606/130 |
| 2010/0168557 A1 | 7/2010 | Deno et al. | |
| 2010/0168571 A1 | 7/2010 | Savery et al. | |
| 2010/0179538 A1 | 7/2010 | Podhajsky | |
| 2010/0274238 A1 | 10/2010 | Klimovitch | |
| 2011/0046618 A1 | 2/2011 | Minar et al. | |
| 2011/0118727 A1 | 5/2011 | Fish et al. | |
| 2011/0130755 A1 | 6/2011 | Bhushan et al. | |
| 2011/0144524 A1 | 6/2011 | Fish et al. | |
| 2011/0152712 A1 | 6/2011 | Cao et al. | |
| 2011/0230876 A1 | 9/2011 | Hong et al. | |
| 2011/0270243 A1 | 11/2011 | Skarda et al. | |
| 2012/0101538 A1 * | 4/2012 | Ballakur | A61B 18/10 607/3 |
| 2012/0116382 A1 * | 5/2012 | Ku | A61B 18/1492 606/33 |
| 2013/0006238 A1 * | 1/2013 | Ditter | A61B 18/1492 606/41 |

FOREIGN PATENT DOCUMENTS

| | | |
|---|---|---|
| EP | 1429678 B1 | 3/2006 |
| EP | 1803410 A1 | 7/2007 |
| EP | 1867279 A3 | 12/2007 |
| EP | 1280467 B1 | 11/2008 |
| WO | 2004011090 A2 | 2/2004 |
| WO | 2011103129 A2 | 8/2011 |

* cited by examiner

SYSTEMS AND METHODS FOR DETECTING TISSUE CONTACT DURING ABLATION

CROSS-REFERENCE TO RELATED APPLICATION

This application is a divisional of patent application Ser. No. 13/460,900, filed May 1, 2012, entitled SYSTEMS AND METHODS FOR DETECTING TISSUE CONTACT DURING ABLATION, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for the detection of tissue contact during treatment or diagnostic procedures.

BACKGROUND OF THE INVENTION

Radiofrequency (RF) and cryogenic ablation procedures are well recognized treatments for vascular and cardiac diseases such as atrial fibrillation. The application of either RF or cryogenic treatment is usually based on the preference of the physician or the specific tissue to be treated. In either RF or cryogenic ablation, however, the location and quality of the lesion produced is a primary concern. The clinical success of cardiac tissue ablation to treat arrhythmias depends on efficacy and safety of the application of the selected energy. In particular, successful treatments may involve successfully ablating problematic tissue while also preventing the transmission of ablative energy to surrounding healthy or otherwise non-targeted tissue.

For example, during procedures such as pulmonary vein ablation or pulmonary vein antrum isolation (PVAI), an ablation device may be used to ablate cardiac tissue surrounding one or more pulmonary veins in the left atrium of the heart. However, ablation extending into the pulmonary veins can contribute to serious complications for the patient, including pulmonary vein stenosis, phrenic nerve injury, and embolic events. Medical imaging modalities provide some aid in assessing the particular location of the ablation device within the patient. However, minimally-invasive ablation procedures are typically performed within a beating heart, and the tortuous, moving cardiac environment presents challenges in accurately locating a targeted tissue and positioning a medical device in place to treat the tissue, even with external imaging systems.

Accordingly, it is desirable to provide systems and methods of use thereof that facilitates accurate positioning of a medical device within a patient for subsequent treatment while avoiding damaging surrounding structures or tissue regions that are not the target of a therapeutic or diagnostic procedure.

SUMMARY OF THE INVENTION

The present invention advantageously provides systems and methods for assessing placement or positioning of one or more electrodes within the body. For example, a method of assessing electrode position is disclosed, including positioning a plurality of electrodes within a heart and proximate a pulmonary vein; obtaining an impedance measurement from each of the plurality of electrodes; determining whether any of the plurality of electrodes is located within the pulmonary vein based at least in part on the obtained impedance measurements; and generating an indication if at least one of the plurality of electrodes is determined to be located within the pulmonary vein. The impedance measurements may be between each of the plurality of electrodes and a ground electrode external to the heart. Determining whether any of the plurality of electrodes is located within the pulmonary vein may include comparing an obtained impedance measurement to a predefined impedance value and/or comparing one of the obtained impedance measurements to another one of the obtained impedance measurements. The method may include comparing an impedance measurement obtained from the plurality of electrodes to impedance measured from an electrode or a plurality of electrodes located on a guide wire or other auxiliary device positioned within the pulmonary vein delivering a non-ablative radiofrequency energy. The guide wire or auxiliary device may be independently delivered to the anatomical region or may be passed through a guide wire lumen provided by a medical device containing the plurality of electrodes.

The method may include preventing ablative energy delivery to an electrode determined to be located within the pulmonary vein. The method may include conducting non-ablative radiofrequency energy through the plurality of electrodes while positioning the electrodes, where the conduction of non-ablative radiofrequency energy may be substantially continuous and/or duty cycled. The non-ablative radiofrequency energy may be conducted between each of the plurality of electrodes and a ground electrode external to the heart and/or conducted between the plurality of electrodes. The method may include conducting non-ablative radiofrequency energy between a plurality of electrodes and skin patches placed on a patient's skin in anterior, posterior, and bilateral positions, allowing differentiation of relative impedances between the plurality of electrodes and the plurality of skin patches. The method may include determining whether any of the plurality of electrodes is located on an antrum of the pulmonary vein based at least in part on the obtained impedance measurements; and generating an indication if at least one of the plurality of electrodes is determined to be located on the antrum of the pulmonary vein, where determining whether any of the plurality of electrodes is located on an antrum of the pulmonary vein may include comparing an obtained impedance measurement to a predefined impedance value. The method may include conducting ablative radiofrequency energy through at least one of the plurality of electrodes, where obtaining an impedance measurement is performed during the conduction of the ablative radiofrequency signal. The generated indication may include visually displaying at least one of 1) a measured impedance value, 2) a calculated difference between a measured impedance value and a predetermined impedance value, and 3) a calculated difference between at least two measured impedance values.

A medical system is disclosed, including a medical device having a plurality of electrodes; a control unit coupled to the medical device, the control unit programmed to: obtain an impedance measurement from each of the plurality of electrodes; determine whether any of the plurality of electrodes is located within the pulmonary vein based at least in part on the obtained impedance measurements; and generate an indication if at least one of the plurality of electrodes is determined to be located within the pulmonary vein. The control unit may determine whether any of the plurality of electrodes is located within the pulmonary vein by comparing an obtained impedance measurement to a predefined impedance value and/or by comparing one of the obtained impedance measurements to another one of the obtained impedance measurements. The control unit may be programmed to prevent ablative energy delivery through an electrode determined to be located within the pulmonary vein.

A method of operating a medical device having an electrode is disclosed, including positioning the electrode adjacent a tissue region; delivering radiofrequency energy to the electrode, wherein the delivered radiofrequency energy is sufficient to ablate at least a portion of the tissue region; obtaining a plurality of impedance measurements from the electrode during the delivery of the radiofrequency energy; calculating a change in the impedance measurements over a pre-determined time period; and generating an alert if the calculated change is less than a pre-defined value. The pre-determined time period may be between approximately 5 seconds and approximately 20 seconds. The method may include terminating delivery of radiofrequency energy to the electrode. The method may include attributing the calculated change in the impedance measurements to a tissue contact condition, where the generated alert signals the tissue contact condition to a user.

A method of operating a medical device having a plurality of electrodes is disclosed, including positioning the plurality of electrodes adjacent a tissue region; delivering radiofrequency energy to each electrode, wherein the delivered radiofrequency energy is sufficient to ablate at least a portion of the tissue region; obtaining a plurality of impedance measurements from each of the plurality of electrodes during the delivery of the radiofrequency energy; calculating a change in the impedance measurements for each of the plurality of electrodes over a pre-determined time period; comparing the calculated change for at least one of the plurality of electrodes to the calculated change in at least one of the other plurality of electrodes; and generating an alert based at least in part on the comparison. The pre-determined time period may be between approximately 5 seconds and approximately 20 seconds, and/or the method may include terminating delivery of radiofrequency energy to at least one of the plurality of electrodes.

A method of operating a medical device having an electrode is disclosed, including delivering radiofrequency energy to the electrode, wherein the radiofrequency energy is delivered in a plurality of successive time fields each having a period and a duty cycle comprising a first portion of the period when ablative radiofrequency energy is being delivered to the electrode and a second portion of the period when ablative radiofrequency energy is not being delivered to the electrode; measuring a first impedance from the electrode during the first portion of the period; measuring a second impedance from the electrode during the second portion of the period; comparing the first and second impedance measurements; and modulating a subsequent duty cycle duration based at least in part on the comparison. The method may include generating an alert based at least in part on the comparison and/or terminating delivery of radiofrequency energy to the electrode based at least in part on the comparison.

A medical system is disclosed, including a medical device having a plurality of electrodes; and a control unit in communication with the plurality of electrodes, the control unit programmed to: deliver radiofrequency energy to the plurality of electrodes, wherein the delivered radiofrequency energy is sufficient to ablate tissue; obtain a plurality of impedance measurements from the plurality of electrodes during the delivery of the radiofrequency energy; calculate a change in the impedance measurements over a pre-determined time period; and generate an alert if the calculated change is less than a pre-defined value. The control unit may be programmed to terminate delivery of radio frequency energy to the electrode, the generated alert may include visually displaying at least one of 1) a measured impedance value, 2) a calculated difference between a measured impedance value and a predetermined impedance value, and 3) a calculated difference between at least two measured impedance values; and/or the control unit may be programmed to attribute the calculated change in the impedance measurements to a tissue contact condition, and the generated alert may signal the tissue contact condition.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
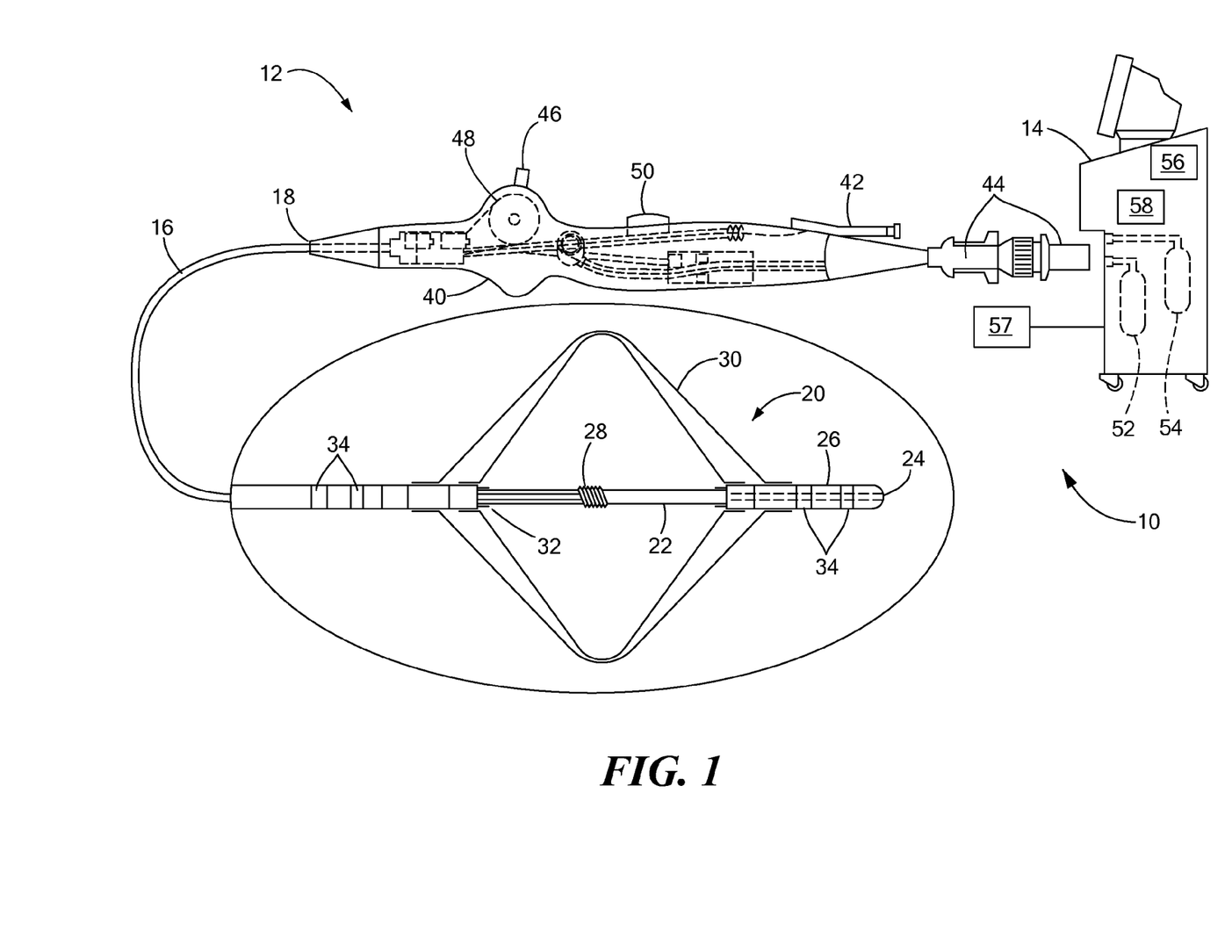
FIG. 1 is an illustration of an example of a medical system constructed in accordance with the principles of the present invention.

The present disclosure advantageously provides a system and methods of use thereof that facilitate accurate positioning of a medical device within a patient for subsequent treatment while avoiding damaging surrounding structures or tissue regions that are not the target of a therapeutic or diagnostic procedure. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12 may generally include one or more diagnostic or treatment regions for energetic, therapeutic and/or investigatory interaction between the medical device 12 and a treatment site. The treatment region(s) may deliver, for example, cryogenic therapy, radiofrequency energy, or other energetic transfer with a tissue area in proximity to the treatment region(s), including cardiac tissue.

Now referring to FIG. 1, the medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16, as discussed in more detail below.

The medical device 12 may include a shaft 22 at least partially disposed within a portion of the elongate body 16. The shaft 22 may extend or otherwise protrude from a distal end of the elongate body 16, and may be movable with respect to the elongate body 16 in longitudinal and rotational directions. That is, the shaft 22 may be slidably and/or rotatably moveable with respect to the elongate body 16. The shaft 22 may further define a lumen 24 therein for the introduction and passage of a guide wire. The shaft 22 may include or otherwise be coupled to a distal tip 26 that defines an opening and passage therethrough for the guide wire.

The medical device 12 may further include a fluid delivery conduit 28 traversing at least a portion of the elongate body and towards the distal portion. The delivery conduit 28 may be coupled to or otherwise extend from the distal portion of the elongate body 16, and may further be coupled to the shaft 22 and/or distal tip of the medical device 12. The fluid delivery conduit 28 may define a lumen therein for the passage or delivery of a fluid from the proximal portion of the elongate body 16 and/or the control unit 14 to the distal portion and/or treatment region of the medical device 12. The fluid delivery conduit 28 may further include one or more apertures or openings therein, to provide for the dispersion or directed ejection of fluid from the lumen to an environment exterior to the fluid delivery conduit 28.

The medical device 12 may further include one or more expandable elements 30 at the distal portion of the elongate body 16. The expandable element 30 may be coupled to a portion of the elongate body 16 and also coupled to a portion of the shaft 22 and/or distal tip 26 to contain a portion of the fluid delivery conduit 28 therein. The expandable element 30 defines an interior chamber or region that contains coolant or fluid dispersed from the fluid delivery conduit 28, and may be in fluid communication with an exhaust lumen 32 defined by or included in the elongate body 16 for the removal of dispersed coolant from the interior of the expandable element 30. The expandable element 30 may further include one or more material layers providing for puncture resistance, radiopacity, or the like.

Figure 2:
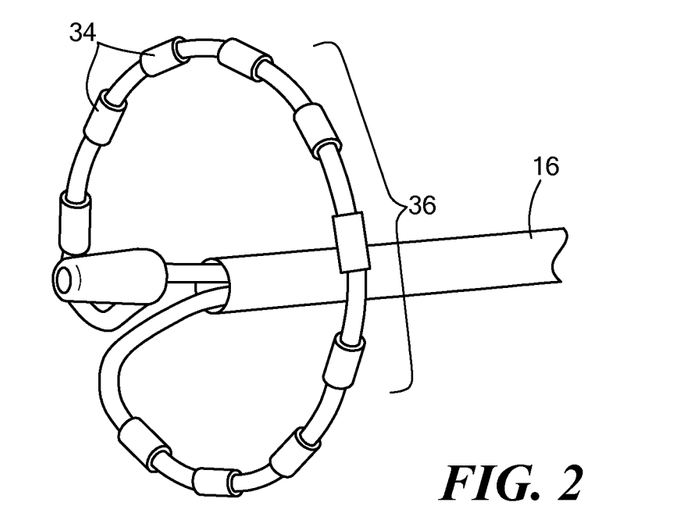
FIG. 2 is an illustration of an example of a medical device assembly constructed in accordance with the principles of the present invention.
Figure 3:
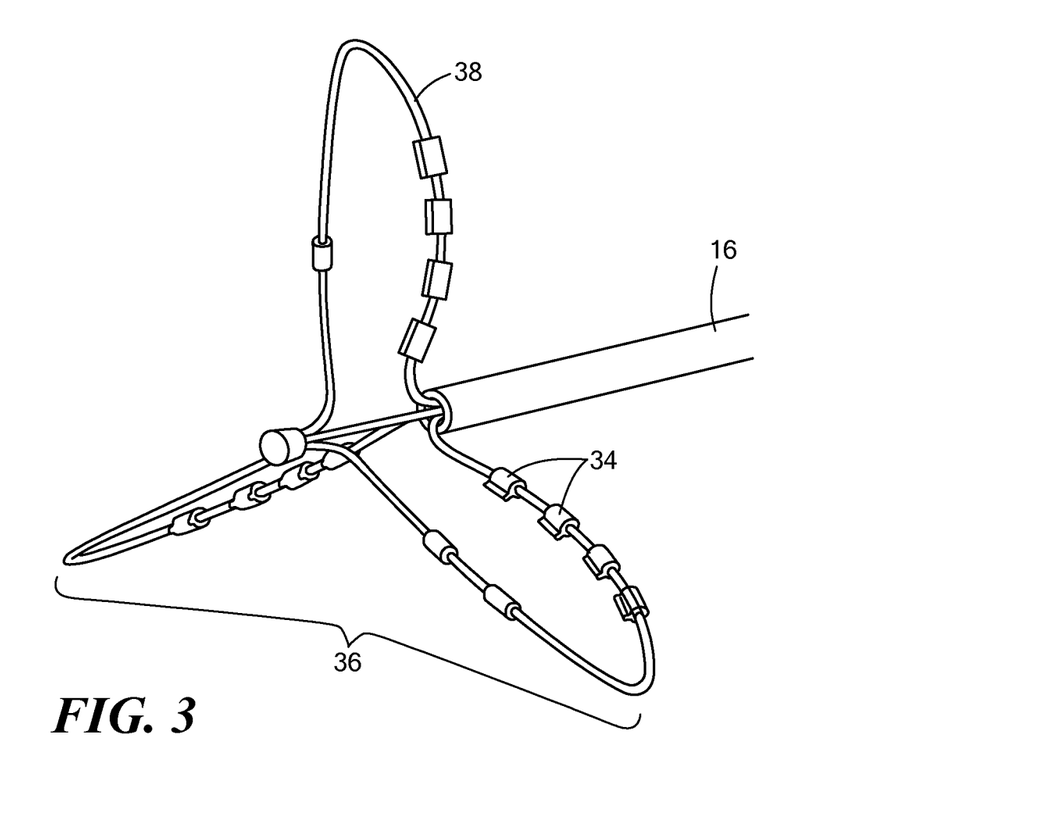
FIG. 3 is another illustration of an example of a medical device assembly constructed in accordance with the principles of the present invention.
Figure 4:
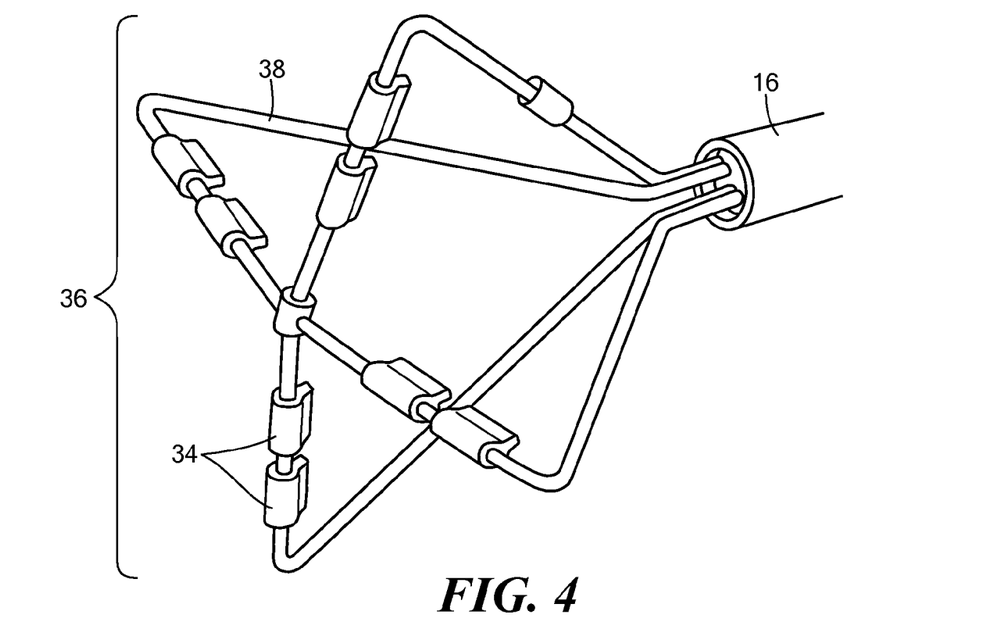
FIG. 4 is still another illustration of an example of a medical device assembly constructed in accordance with the principles of the present invention.
Figure 5:
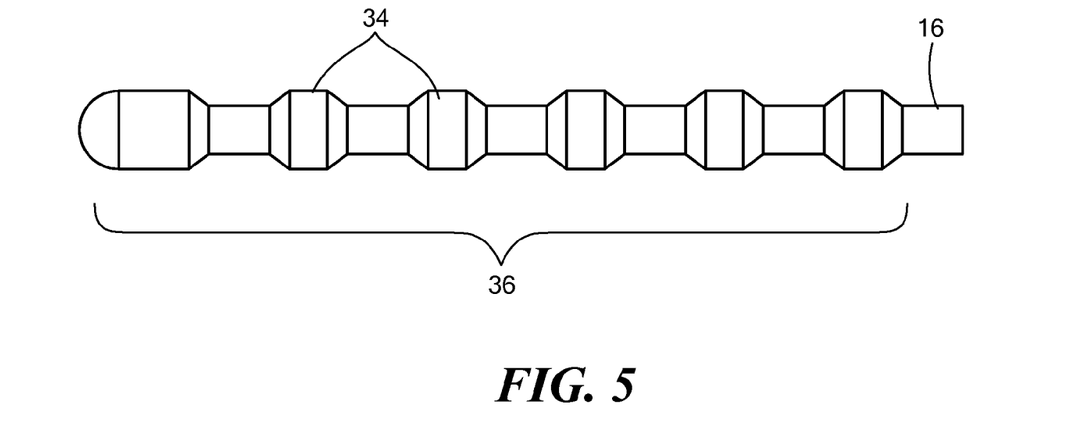
FIG. 5 is yet another illustration of an example of a medical device assembly constructed in accordance with the principles of the present invention.

The medical device 12 may further include one or more electrically-conductive segments or electrodes 34 positioned on or about the elongate body for conveying an electrical signal, current, or voltage to a designated tissue region and/or for measuring, recording, or otherwise assessing one or more electrical properties or characteristics of surrounding tissue. The electrodes 34 may be configured in a myriad of different geometric configurations or controllably deployable shapes, and may also vary in number to suit a particular application, targeted tissue structure or physiological feature. For example, as shown in FIG. 1, the electrodes 34 may include a first pair proximate to the expandable element and a second electrode pair distal to the expandable element. Alternative electrode configurations of the medical device 12 are illustrated in FIGS. 2-5. FIG. 2 includes an electrode array 36 configurable into a looped or substantially circular configuration. The electrode array 36 in FIG. 3 includes a plurality of arms 38, with the electrodes 34 positioned in a proximal-facing direction or orientation on the arms 38. FIG. 4 also includes a plurality of extendable or deployable arms 38 having a plurality of electrodes 34 in a square-like or "X"-shaped configuration. Turning to FIG. 5, a plurality of electrodes 34 are shown in a substantially linear array 36 extending along a portion of the elongate body 16 of the medical device 12. Additional details related to the configurations, manipulation, and exemplary uses of the electrode configurations shown in FIGS. 2-5 are provided in U.S. patent application Ser. No. 12/116,753, filed on May 7, 2008, entitled "Ablation Therapy System and Method for Treating Continuous Atrial Fibrillation," the entirety of which is hereby incorporated by reference.

Each electrode 34 may be electrically coupled to an output portion of a radiofrequency signal generator, and each electrode 34 may also include a sensor, such as a thermocouple, an electrical conductivity sensor, a spectrometer, a pressure sensor, a fluid flow sensor, a pH sensor, and/or a thermal sensor (not shown) coupled to or in communication with the electrodes. The sensors may also be in communication with a feedback portion of the control unit 14 to trigger or actuate changes in operation when predetermined sequences, properties, or measurements are attained or exceeded.

Referring again to FIG. 1, the medical device 12 may include a handle 40 coupled to the proximal portion of the elongate body 16. The handle 40 can include circuitry for identification and/or use in controlling of the medical device 12 or another component of the system. Additionally, the handle 40 may be provided with a fitting 42 for receiving a guide wire that may be passed into the guide wire lumen 24. The handle 40 may also include connectors 44 that are matable to the control unit 14 to establish communication between the medical device 12 and one or more components or portions of the control unit 14.

The handle 40 may also include one or more actuation or control features that allow a user to control, deflect, steer, or otherwise manipulate a distal portion of the medical device 12 from the proximal portion of the medical device 12. For example, the handle 40 may include one or more components such as a lever or knob 46 for manipulating the elongate body 16 and/or additional components of the medical device 12. For example, a pull wire 48 with a proximal end and a distal end may have its distal end anchored to the elongate body 16 at or near the distal portion 20. The proximal end of the pull wire 48 may be anchored to an element such as a cam in communication with and responsive to the lever 46. The medical device 12 may include an actuator element 50 that is movably coupled to the proximal portion of the elongate body 16 and/or the handle 40 for the manipulation and movement of a portion of the medical device 12, such as the shaft 22, and/or one or more portions of the electrode assemblies described above, for example.

The system 10 may include one or more treatment sources coupled to the medical device for use in an operative procedure, such as tissue ablation, for example. The control unit 14 may include a fluid supply 52 including a coolant, cryogenic refrigerant, or the like, an exhaust or scavenging system (not shown) for recovering or venting expended fluid for re-use or disposal, as well as various control mechanisms. In addition to providing an exhaust function for the fluid or coolant supply 52, the control unit 14 may also include pumps, valves, controllers or the like to recover and/or re-circulate fluid delivered to the handle 40, the elongate body 16, and/or the fluid pathways of the medical device 12. A vacuum pump 54 in the control unit 14 may create a low-pressure environment in one or more conduits within the medical device 12 so that fluid is drawn into the conduit(s)/lumen(s) of the elongate body 16, away from the distal portion 20 and towards the proximal portion 18 of the elongate body 16.

The control 14 unit may include a radiofrequency generator or power source 56 as a treatment or diagnostic mechanism in communication with the electrodes 34 of the medical device 12. The radiofrequency generator 56 may have a plurality of output channels, with each channel coupled to an individual electrode 34. The radiofrequency generator 56 may be operable in one or more modes of operation, including for example: (i) bipolar energy delivery between at least two electrodes on the medical device within a patient's body, (ii) monopolar or unipolar energy delivery to one or more of the electrodes 34 on the medical device 12 within a patient's body and through a patient return or ground electrode 57 spaced apart from the electrodes 34 of the medical device 14, such as on a patient's skin or on an auxiliary device (such a guide wire or secondary catheter) within the patient, for example, and (iii) a combination of the monopolar and bipolar modes.

The signal provided by the radiofrequency generator or power source 56 may be substantially continuous or include duty cycles of on/off periods of energy delivery. As used herein, the term "duty cycle" refers to the proportion of time during which a component, device or system is operated to achieve a desired effect. The duty cycle can be expressed as a ratio or as a percentage, e.g., 1/10 denotes 1 "on" period per ten total periods, or a 10% duty cycle. As used herein, the term "field" refers to a single period of a duty cycle. Each field includes an "on" time in which energy is delivered to achieve a desired effect (such as ablating tissue) and an "off" time in which little or no energy is delivered. Of note, the "off" period may include some conduction or transfer of energy, but not in sufficient amounts to achieve the effect of the "on" period. In a particular example, the radiofrequency generator 56 may have a plurality of output channels each having a sequential set of fields (e.g. 2, 4, 8) providing a customized power delivery scheme which repeats and/or dynamically changes over time in response to one or more monitored or measured parameters of the system, a patient, and/or procedure being performed. Additional details related to the configurations and exemplary uses of the system 10 and radiofrequency generator or power source 56 discussed herein are provided in U.S. patent application Ser. No. 12/117,596, filed on May 8, 2008, entitled "RF Energy Delivery System 10 and Method," the entirety of which is hereby incorporated by reference.

The control unit 14 may include an impedance measurement module or signal processing unit 58 to measure one or more impedance characteristics between the electrodes of the medical device. As used herein, the term impedance refers to the generally accepted definition of the term: a complex ratio of sinusoidal voltage to current in an electric circuit or component, except that as used herein, impedance shall apply to any region or space through which some electrical field is applied and current flows. The impedance, Z, may be expressed as a complex number, $Z=R+jX$, wherein R is the resistance in real number ohms, X is the reactance in imaginary number ohms, and j is a multiplier that is the positive square root of negative one (−1). Impedance may also be expressed in polar form as $Z=|Z|e^{j\theta}$, where |Z| is the magnitude (e.g., the ratio of the voltage difference amplitude to the current amplitude), θ is the phase difference between voltage and current, and j is the imaginary unit. An excitation current may be applied between one or more of the electrodes 34 on the medical device 12 and/or a patient return or ground electrode 57, and the resulting impedance may be monitored or measured, as described in more detail below. Alternatively, a plurality of electrodes may be situated about the patient (such as on skin patches or otherwise) placed on the patient's skin in anterior, posterior, and bilateral positions, allowing differentiation of relative impedances between the plurality of electrodes on the medical device and the plurality of electrodes/skin patches. Excitation and the resulting measurements for impedance parameters may continue or otherwise be repeated until impedance measurements are calculated for various combinations of electrodes before, during and/or after a designated procedure.

The system 10 may further include one or more sensors to monitor the operating parameters throughout the system, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14. The control unit 14 may include one or more controllers, processors, and/or software modules containing instructions or algorithms to provide for the automated operation and performance of the features, sequences, calculations, or procedures described herein.

Figure 6:
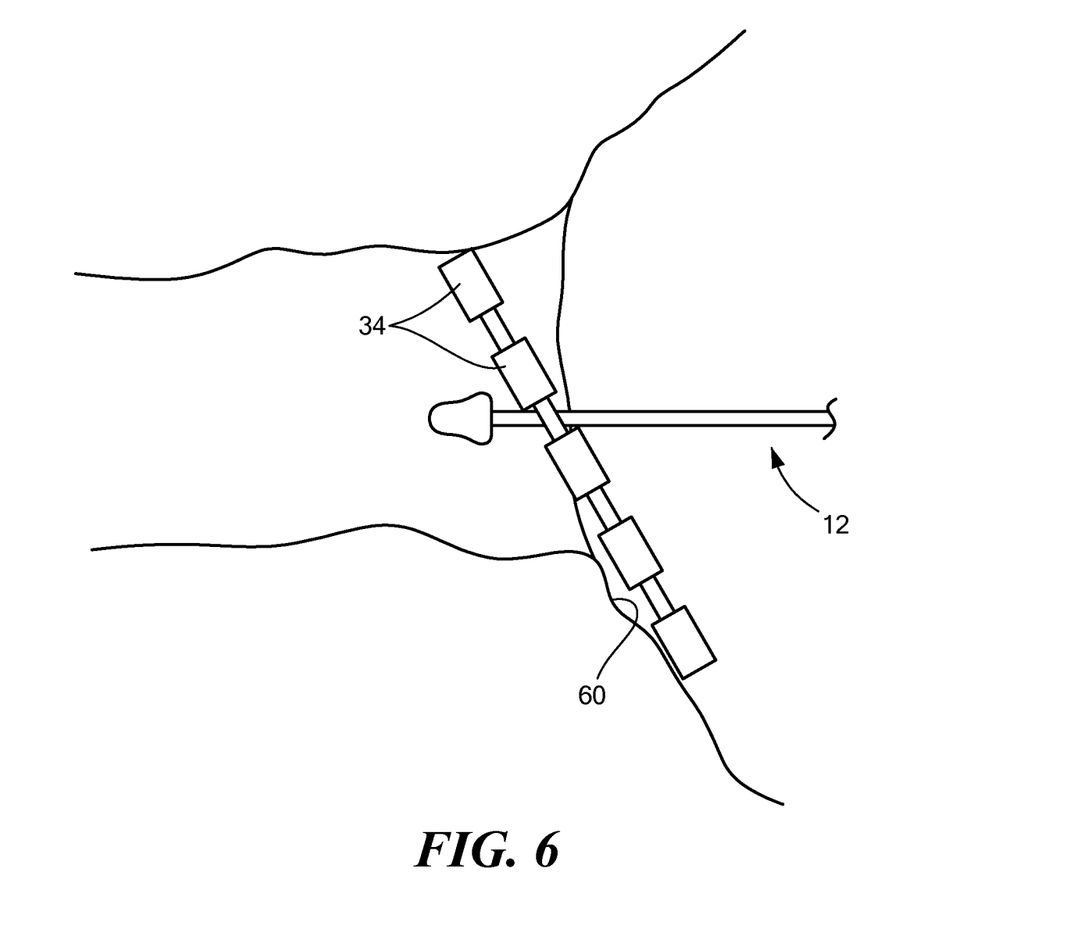
FIG. 6 is an illustration of an example of using a medical system in accordance with the principles of the present invention.
Figure 7:
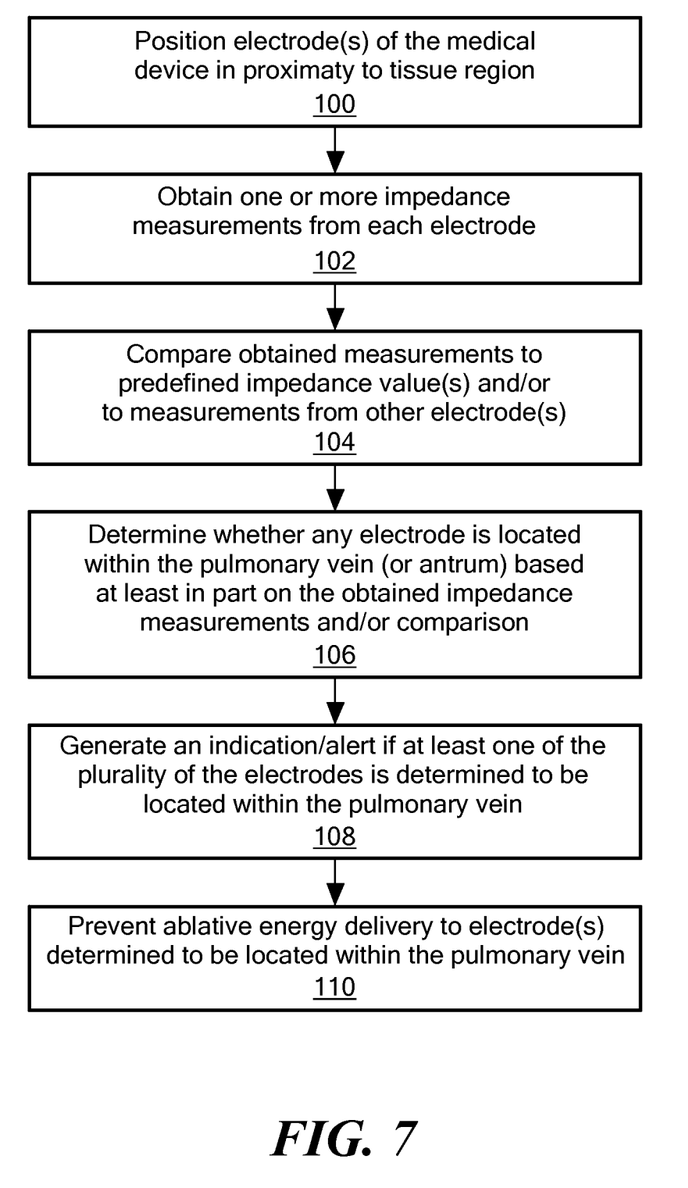
FIG. 7 is a flow chart of an exemplary method of operating a medical device in accordance with the principles of the present invention.

Now referring to FIGS. 6-7, exemplary methods of use of the system described herein are disclosed. In particular, impedance may be measured and/or monitored and used as a basis for determining tissue type, electrode location, and/or contact between an electrode and a tissue region. Measured impedances may also be used to dynamically modulate or adjust energy delivery to one or more of the electrodes during treatment.

For example, impedance across pulmonary vein tissue is considerably higher than impedance across the cardiac tissue of the antrum of a pulmonary vein within the left atrium of the heart. Accordingly, measured impedance differences between one or more electrodes 34 of the device 12 may be used as a basis to generate an alert that at least a portion of the medical device is undesirably placed too far within a pulmonary vein. Particularly referring to FIGS. 6 and 7, one or more of the electrodes 34 the medical device 12 may be positioned in proximity to a tissue region 60 targeted for a diagnostic or therapeutic procedure (Step 100), which may include tissue ablation for the treatment of atrial fibrillation or other condition. The tissue region 60 may include a pulmonary vein opening and antrum in the left atrium, for example. Once positioned, one or more impedance measurements may be taken or obtained from each of the electrode(s) (Step 102). The impedance measurements may be obtained by directing sufficient current from the radiofrequency generator 56 to one or more of the electrodes 34 of the medical device 12 to obtain an impedance value between 1) two or more electrodes on the medical device; 2) between one or more of the electrodes on the medical device 12 and the ground electrode 57; 3) between one or more of the electrodes on the medical device 12 and one or more of a plurality of electrodes external to the heart; and/or 4) between one or more of the electrodes on the medical device 12 and one or more of a plurality of electrodes of an auxiliary device, such as a guide wire or secondary catheter. The energy conducted through the electrodes for the impedance measurements may be significantly less than an energy level that would ablate or damage the tissue and does not cause cardiac stimulation. For example, the non-ablative energy may include alternating current energy at a frequency of approximately 10 kHz having a voltage less than approximately 1 volt. The delivery of such non-ablative energy may be substantially continuous during placement of the medical device, or may be duty-cycled. The non-ablative, non-stimulating energy may further be delivered at a plurality of frequencies in sequential bursts or duty-cycled durations of energy conductance. The impedance measurements may be recorded, processed, and/or stored by the impedance measurement module 58 in the control unit 14, for example. Examples of multi-frequency energy delivery and corresponding impedance measurements are provided in U.S. patent application Ser. No. 13/017,122, filed on Jan. 31, 2011, the entirety of which is hereby incorporated by reference.

Upon obtaining one or more of the impedance measurements, the obtained measurements from each electrode may then be compared to a pre-defined impedance value (which may include an expected impedance value for atrial tissue and/or an expected value for pulmonary vein tissue). Additionally or alternatively, the measurements of each electrode may be compared to the measurements from the other electrodes, and a difference or variation between the electrodes may be processed or calculated (Step 104). A determination whether any of the electrodes 34 are located within the pulmonary vein may be made based at least in part on the obtained impedance measurements and/or comparison of the obtained values (Step 106). A determination whether any of the electrodes 34 are located on an antrum or atrial wall may be made based at least in part on the obtained impedance measurements and/or comparison of the obtained values. The determination may be performed by one or more processors of the control unit 14 and/or the impedance measurement module 58. If one or more of the electrodes 34 of the medical device 12 are determined to extend into an undesirable depth of the pulmonary vein, the control unit 14 may generate an indication or alert of such positioning (Step 108). The generated indication or alert may include, for example, visually displaying at least one of 1) a measured impedance value, 2) a calculated difference between a measured impedance value and a predetermined impedance value, and/or 3) a calculated difference between at least two measured impedance values. The generated indication or alert may additionally or alternatively include one or more audible indications as well.

The determination of whether any electrode is located within the pulmonary vein may also result in deactivating or preventing ablative energy form being transmitted or conducted through the electrode(s) determined to be in the pulmonary vein (Step 110). One or more electrode(s) not determined to be within the pulmonary vein may then proceed to be used for the procedure at hand, which may include delivering or conducting ablative energy through the electrode(s) in a desired position or location on the antrum and/or atrium wall. Additionally, impedance measurements may be obtained, processed, and compared as described above during the conduction of the ablative radiofrequency signal to prevent or signal an unwanted change in electrode position during a procedure, e.g., if any of the active electrodes migrate into the pulmonary vein while ablating.

Changes in measured impedances may also be used to indicate contact between one or more of the electrodes 34 and the targeted tissue region 60. For example, impedance measurements are higher when a treatment element is in contact with tissue than when a treatment element is not in contact with tissue but rather surrounded by blood within vasculature. Moreover, during energy delivery to targeted tissue, electrodes lacking quality contact with tissue will show a relatively stable impedance value, whereas electrodes in good tissue contact will show an impedance reduction during initial energy delivery to the tissue. Accordingly, in addition to the impedance measurements providing positioning information as described above, the measured impedance values may also be used to indicate whether electrodes used in treating tissue have maintained or lost their contact. In particular, upon delivering ablative radiofrequency energy to one or more electrodes (such as those found to be on an antrum and not in the pulmonary vein, for example), the control unit 14 and/or impedance measurement module 58 may continue obtaining a plurality of impedance measurements from each electrode during the delivery of the radio frequency energy. The control unit 14 and/or impedance measurement module 58 may calculate a change in the impedance measurements over a pre-determined time period, which may be between approximately 5 seconds and approximately 20 seconds, for example. The calculated change may include an absolute value, or the calculated change may include an average rate of change.

The control unit 14 and/or impedance measurement module 58 may then generate an alert or indication if the calculated change (or rate of change) is less than (or greater than) a pre-defined value or otherwise fails to fall within a defined, acceptable range of values at any time during a procedure. Additionally or alternatively, the control unit 14 and/or impedance measurement module 58 may compare impedance changes between electrodes to determine whether there is any significant variation in the measured rates of change for each electrode, which indicates that the electrodes are not in sufficient contact with the targeted tissue. The control unit 14 and/or radiofrequency generator 56 may subsequently terminate delivery of radiofrequency energy to the electrode as a result of the calculation and comparison of impedance changes.

Changes in measured impedances may also be used to modulate or regulate duty cycles for power delivery to one or more of the electrodes 34. For example, the control unit 14 and/or impedance measurement module 58 may monitor the impedance between each electrode of the medical device 12 and the ground electrode 57 during duty cycled energy delivery; monitor impedance to the ground electrode 57 during the "on" periods of duty cycled delivery where therapeutic or ablative energy levels are being delivered; monitoring impedance to the ground electrode 57 during the "off" periods of duty cycled delivery where during the off periods, the driving voltage of the phased radiofrequency energy is not zero but is at a level that allows impedance measurement without ablating tissue; and/or monitor impedance during the off periods where the non-zero level of energy is totally unipolar, regardless of the mode of delivery during the on periods (of note, there may be bipolar components delivered during the "on" periods due to out of phase condition between individual electrodes). The control unit 14 and/or impedance measurement module 58 may compare impedance measurements made during the "on" and "off" periods of duty cycled energy delivery and modulate the duty cycle durations based at least in part on measured changes in relative impedance.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of operating a medical device having a plurality of electrodes, comprising:
   - positioning the plurality of electrodes adjacent a tissue region;
   - delivering radiofrequency energy to each of the plurality of electrodes, wherein the delivered radiofrequency energy is sufficient to ablate at least a portion of the tissue region;
   - obtaining a plurality of impedance measurements from each of the plurality of electrodes during the delivery of the radiofrequency energy;
   - calculating a change in the impedance measurements for each of the plurality of electrodes over a pre-determined time period;
   - comparing the calculated change for at least one of the plurality of electrodes to the calculated change for at least one of the other plurality of electrodes; and
   - terminating the delivery of radiofrequency energy to at least one of the plurality of electrodes based at least in part on the comparison.

2. The method of claim 1, further comprising:
   - attributing the calculated change in the impedance measurements to a tissue contact condition; and
   - generating an alert that signals the tissue contact condition.

3. The method of claim 1, wherein the pre-determined time period is between approximately 5 seconds and approximately 20 seconds.

4. The system of claim 1, wherein each of the plurality of electrodes includes a sensor.

* * * * *